(12) United States Patent
Cordell et al.

(10) Patent No.: US 6,428,950 B1
(45) Date of Patent: Aug. 6, 2002

(54) ASSAY TO IDENTIFY COMPOUNDS THAT ALTER APOLIPOPROTEIN E EXPRESSION

(75) Inventors: Barbara Cordell, Palo Alto; Qiang Xu, Cupertino; Asha Naidu, Fremont, all of CA (US); Steven M. Paul, Carmel; Kelly R. Bales, Cloverdale, both of IN (US)

(73) Assignees: Scios Inc., Sunnyvale, CA (US); Eli Lilly & Co., Indianapolis, IN (US)

( * ) Notice: Subject to any disclaimer, the term of this patent is extended or adjusted under 35 U.S.C. 154(b) by 0 days.

(21) Appl. No.: 09/447,452

(22) Filed: Nov. 22, 1999

Related U.S. Application Data

(60) Provisional application No. 60/109,910, filed on Nov. 25, 1998.

(51) Int. Cl.$^7$ .......................... C12Q 1/00; G01N 33/567; C12P 21/04; A61K 35/30; A61K 35/12

(52) U.S. Cl. .......................... 435/4; 435/7.21; 435/70.3; 424/570; 424/572; 424/577; 514/1

(58) Field of Search .............................. 424/562; 435/4, 435/7.21, 70.3; 514/1

(56) References Cited

PUBLICATIONS

Mouchel et al. Apolipoprotein E gene expression in astrocytes: developmental pattern and regulation. NeuroReport, 1995, 7, pp. 205–207.*

Stone et al. Astroctes and microglia respond to estrogen with increased apoE mRNA in Vivo and In Vitro. Exp.Neurology, 1997, 143, pp313–318.*

Boyles et al. (Oct. 1985), "Apolipoprotein E Associated with Astrocytic Glia of the Central Nervous System and with Nonmyelinating Glia of the Peripheral Nervous System," *J. Clin. Invest.*, vol. 76:1501–1513.

Corder et al. (Aug. 13, 1993), "Gene Dose of Apolipoprotein E Type 4 Allele and the Risk of Alzheimer's Disease in Late Onset Families," *Science*, vol. 261:933–923.

Clark et al. (Nov. 1993), "Molecular Genetics of Alzheimer's Disease," *Arch Neurol.*, vol. 50:1164–1172.

Crowther (1993), "Tau Protein and Paired Helical Filaments of Alzheimer's Disease," *Curr. Opin. in Structural Biol.*, vol. 3:202–206.

Khoury et al. (1998), "Microglia, Scavenger Receptors, and the Pathogenesis of Alzheimer's Disease," *Neurobiology of Aging*, vol. 19(18):S81–S84.

Elshourbagy et al. (Jan. 1985), "Apolipoprotein E mRNA is Abundant in the Brain and Adrenals, as well as in the Liver, and is present in Other Peripheral Tissues of Rats and Marmosets," *Proc. Natl. Acad. Sci. USA*, vol. 82:203–207.

Glenner et al. (1989), "Amyloidosis of the Nervous System," *Journal of the Neurological Sciences*, vol. 94:1–28.

Goodison et al. (May 1993), "Neuronal and Glial Gene Expression in Neocortex of Down's Syndrome and Alzheimer's Disease," *J. of Neuropathology and Experimental Neurology*, vol. 52(3):193–198.

Greenberg et al. (Oct. 1993), "The Clinical Spectrum of Cerebral Amyloid Angiopathy: Presentations Without Lobar Haemorrhage," *Neuroloby*, vol. 43:2073–2079.

Hardy (1997), "Amyloid, the Presenilins and Alzheimer's Disease," *TINS*, vol. 20(4):154–159.

Haan et al. (1990), "Amyloid in Central Nervous System Disease," *Clin. Neurol. Neurosurg.*, vol. 92–4:305–310.

Hardy (May 1994), "Alzheimer's Disease–Clinical Molecular Genetics," *Clinics in Geriatric Medicine*, vol. 10(2):239–247.

Hu et al. (1998) Accession No. 626154 "Apolipoprotein E Attenuates β– Amyloid Induced Astrocyte Activation."

Ignatius et al. (Feb. 1986), "Expression of Apolipoprotein E During Nerve Degeneration and Regeneration," *proc. Natl. Acad. Sci. USA*, vol. 83:1125–1129.

Itoh et al. (1993), "Cerebral Amyloid Angiopathy: A Significant Cause of Cerebellar as Well as Lobar Cerebral Hemorrhage in the Elderly," *Journal of the Neurological Sciences*, vol. 116:135–141.

Kalaria et al. (Feb. 1995), "Differential Degeneration of the Cerebral Microvascular in Alzheimer's Disease," *NeuroReport*, vol. 6:477–480.

Kawai et al. (1993), "Degeneration of Vascular Muscle Cells in Cerebral Amyloid Angiopathy of Alzheimer's Disease," *Brain Research*, vol. 623:142–146.

Krul et al. (1992) Accession No. 445222, "Secretion of Apolipoprotein E by an Astrocytoma Cell Line."

Lannfelt et al. (Sep. 27, 1993), "Amyloid Precursor Protein Gene Mutation at Codon 670/671 in Familial Alzheimer's Disease in Sweden," *Biochemistry of Neurodegenerative Disorders*, pp. 176–179.

(List continued on next page.)

*Primary Examiner*—John Ulm
*Assistant Examiner*—Olga N. Chernyshev
(74) *Attorney, Agent, or Firm*—Karl Bozicevic; James S. Keddie; Bozicevic, Field & Francis LLP

(57) ABSTRACT

The present invention provides a method of assaying for and arresting, preventing and/or reversing the impairment of central and peripheral nervous system function comprising reducing β-amyloid plaque burden by the administration of compounds that reduce apoE expression. The compounds used in the method of the invention may be: 1) inhibitors of 3-hydroxy-3-methylglutaryl coenzyme A (HMG CoA) reductase; 2) inhibitors of cholesterol biosynthesis; 3) inhibitors of protein isoprenylation, specifically geranylgeranylation; and/or 4) inhibitors of NF-κB activation or function. Assays for compounds with inhibit apoE expression from microglial cells are also disclosed.

2 Claims, 7 Drawing Sheets

PUBLICATIONS

Lendon et al. (Mar. 12, 1997), "Exploring the Etiology of Alzheimer Disease Using Molecular Genetics," *JAMA*, vol. 277(10):825–831.

Levy et al. (Jun. 1990), "Mutation of the Alzheimer's Disease Amyloid Gene in Hereditary Cerebral Hemorrhage, Dutch Type," *Science*, 248:1124–1126.

Maat–Schieman et al. (1994), "Hereditary Cerebral Hemorrhage with Amyloidosis (Dutch): a Model for Congophilic Plaque Formation without Neurofibrillary Pathology," *Acta Neuropathol.*, vol. 88:371–378.

Mahley (Apr. 1998), "Apolipoprotein E: Cholesterol Transport Protein with Expanding Role in Cell Biology," *Science*, vol. 240:622–630.

Mandybur (1989), "Cerebral Amyloid Angiopathy and Astrocytic Gliosis in Alzheimer's Disease," *Acta Neuropathol*, vol. 78:329–331.

Mann et al. (1992), "The Time Course of Pathological Events in Down's Syndrome with Particular Reference to the Involvement of Microglial Cells and Deposits of β/A4," *Neurodegeneration*, vol. 1:201–215.

Martin et al. (Dec. 1994), "Synaptic Pathology and Glial Responses to Neuronal Injury Precede the Formation of Senile Plaques and Amyloid Deposits in the Aging Cerebral Cortex," *American Journal of Pathology*, vol. 145(6):1358–1381.

Masliah et al. (Sep. 15, 1996), "Comparison of Neurodegenerative Pathology in Transgenic Mice Overexpressing V717F β–Amyloid Precursor Protein and Alzheimer's Disease," *Journal of Neurosciences*, vol. 16(18):5795–5811.

McKhann et al. (Jul. 1984), "Clinical Diagnosis of Alzheimer's Disease: Report of the NINCDS–ADRDA Work Group Under the Auspices of Department of Health and Human Services Task Force on Alzheimer's Disease," *Neurology*, vol. 34:939–944.

Messmer–Joudrier et al. (1996), "Injury–Induced Synthesis and Release of Apolipoprotein E and Clusterin from Rat Neural Cells," *European Journal of Neuroscience*, vol. 8:2652–2661.

Müller et al. (Apr. 1985), "A Specific 37,000–Dalton Protein that Accumulates in Regenerating but not in Nonregenerating Mammalian Nerves," *Science*, vol. 228:499–501.

Müller et al. (1998) Accession No. 699100, "Apolipoprotein E Isoforms Increase Intracellular Ca2+ Differentially Through a Omega –Agatoxin IVa–Sensitive Ca2+–Channel."

Oyama et al. (1994), "Down's Syndrome: Up Regulation of β–Amyloid Protein Precursor and T mRNA's and Their Defective Coordination," *Journal of Neurochemistry*, vol. 62(3):1062–1066.

Pike et al. (1995), "Structure–Activity Analysis of β–Amyloid Peptides: Contributions of the β25–35 Region to Aggregation and Neurotoxicity," *Journal of Neurochemistry*, vol. 34:253–265.

Pitas et al. (1987), "Lipoproteins and Their Receptors in the Central Nervous System," *Journal of Biological Chemistry*, vol. 262(29):14352–14360.

Pitas et al. (1987), "Astrocytes Synthesize Apolipoprotein E and Metabolize Apolipoprotein E–Containing Lipoproteins," *Biochimica et Biophysica Acta*, vol. 917:148–161.

Reed et al. (Dec. 1994), "Lower Cognitive Performance in Normal Older Adult Male Twins Carrying the Apolipoprotein E є4 Allele," *Arch Neurol.*, vol. 51:1189–1192.

Roses (1994), "The Alzheimer's Diseases," *Current Neurology*, vol. 14:111–141.

Saunders et al. (Aug. 1993), "Association of Apolipoprotein E Allele є4 with Late–Onset Familial and Sporadic Alzheimer's Disease," *Neurology*, vol. 43:1467–1472.

Selkoe (1993), "Physiological Production of the β–Amyloid Protein and the Mechanism of Alzheimer's Disease," *TINS*, vol. 16(10):403–409.

Selkoe (Apr. 1991), "The Molecular Pathology of Alzheimer's Disease," *neuron*, vol. 6:487–498.

Selkoe (Aug. 1998), "Amyloid β–Protein and the Genetics of Alzheimer's Disease," *Journal of Biological Chemistry*, vol. 271(31):18295–18298.

Selkoe et al. (Oct. 1998), "β–Amyloid Precursor Protein of Alzheimer Disease Occurs as 110–to 135– Kilodalton membrane –Associated Proteins in Neural and Nonneural Tissues," *Proc. Natl. Acad. Sci USA*, vol. 85:7341–7345.

Terry et al. (1994), "Structural Basis of the Cognitive Alterations in Alzheimer's Disease," *Alzheimer Disease*, Chapter 11:179–196.

Vinters (Mar.–Apr. 1987), "Cerebral Amyloid Angiopathy: A Critical Review," *Stroke*, vol. 18(2):311–324.

Wattendorff et al. (1995), "Hereditary Cerebral Haemorrhage with Amyloidosis, Dutch Type (HCHWA–D) Clinicopathological Studies," *Journal of Neurology, Neurosurgery, and Psychiatry*, vol. 58:699–705.

Weisgraber et al. (1994), "Lipoproteins, Neurobiology, and Alzheimer's Disease: Structure and Function of Apolipoprotein E," *Current Opinion in Structural Biology*, vol. 4:507–515.

Weisgraber et al. (1994), "The Role of Apolipoprotein E in the Nervous System," *Current Opinion in Lipidology*, vol. 5:110–116.

Wisniewski et al. (Mar. 1985), "Occurrence of Neuropathological Changes and Dementia of Alzheimer's Disease in Down's Syndrome," *Annals of Neurology*, vol. 17(3):278–282.

Yamada et al. (1993), "Subarachnoid Haemorrhage in the Elderly: A Necropsy Study of the Association with Cerebral Amyloid Angiopathy," *Journal of Neurology, Neurosurgery and Psychiatry*, vol. 56:543–547.

Yanker (Aug. 1996), "New Clues to Alzheimer's Disease: Unraveling the Roles of Amyloid and Tau," *Nature Medicine*, vol. 2(8):850–852.

Mahley, Robert W. (1997) "Apolipoprotein E: Structure and Function in Lipid Metabolism and Neurobiology." In *The Molecular and Genetic Basis and Neurological Disease*, Rosenberg et al., eds. Chapter 60 p. 1037–1049.

* cited by examiner

ASSAY TO IDENTIFY COMPOUNDS THAT ALTER APOLIPOPROTEIN E EXPRESSION

CROSS-REFERENCE TO RELATED APPLICATIONS

This application claims priority under 35 U.S.C. §119(e) to U.S. Provisional Application No. 60/109,910, filed Nov. 25, 1998.

FIELD OF THE INVENTION

The invention relates generally to the diagnosis and treatment of neurological diseases and specifically to determining if a patient's microglial and/or astrocyte cells are expressing apoE and suppressing such expression.

BACKGROUND OF THE INVENTION

A number of important neurological diseases including Alzheimer's disease (AD), cerebral amyloid angiopathy (CAA), and prion-mediated diseases are characterized by the deposition of aggregated proteins, referred to as amyloid, in the central nervous system (CNS) (for reviews, see Glenner et al. (1989) *J. Neurol. Sci.* 94:1–28; Haan et al. (1990) *Clin. Neurol. Neurosurg.* 92(4):305–310. These highly insoluble aggregates are composed of nonbranching, fibrillar proteins with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) *Neuroreport* 6:477–80; Masliah et al. (1996) *J. Neurosci.* 16:5795–5811). AD studies additionally indicate that amyloid fibrils may actually initiate neurodegeneration (Lendon et al. (1997) *J. Am. Med. Assoc.* 277:825–31; Yankner (1996) *Nat. Med.* 2:850–2; Selkoe (1996) *J. Biol. Chem.* 271:18295–8; Hardy (1997) *Trends Neurosci.* 20:154–9).

AD and CAA share biochemical and neuropathological markers, but differ somewhat in the extent and location of amyloid deposits as well as in the symptoms exhibited by affected individuals. The neurodegenerative process of AD, the most common cause of progressive intellectual failure in aged humans, is characterized by the progressive and irreversible deafferentation of the limbic system, association neocortex, and basal forebrain accompanied by neuritic plaque and tangle formation (for a review see Terry et al. (1994) "Structural alteration in Alzheimer's disease." In: Alzheimer's disease (Terry et al. eds.), pp. 179–196. Raven Press, New York). Dystrophic neurites, as well as reactive astrocytes and microglia, are associated with these amyloid-associated neurite plaques. Although, the neuritic population in any given plaque is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy (1997) *Trends Neurosci.* 20:154–9; Haan et al. (1990) *Clin. Neurol. Neurosurg.* 92:305–10; Terry et al., supra; Vinters (1987) *Stroke* 18:211–24; Itoh et al. (1993) *J. Neurological Sci.* 116:135–41; Yamada et al. (1993) *J. Neurol. Neurosurg. Psychiatry* 56:543–7; Greenberg et al. (1993) *Neurology* 43:2073–9; Levy et al. (1990) *Science* 248:1124–6). In some familial CAA cases, dementia was noted before the onset of hemorrhages, suggesting the possibility that cerebrovascular amyloid deposits may also interfere with cognitive functions.

In both AD and CAA, the main amyloid component is the amyloid β protein (Aβ). The Aβ peptide, which is generated from the amyloid β precursor protein (APP) by two putative secretases, is present at low levels in the normal CNS and blood. Two major variants, $A\beta_{1-40}$ and $A\beta_{1-42}$, are produced by alternative carboxy-terminal truncation of APP (Selkoe et al. (1988) *Proc. Natl. Acad. Sci. USA* 85:7341–7345; Selkoe, (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

The precise mechanisms by which neuritic plaques are formed and the relationship of plaque formation to the AD-associated, and CAA-associated neurodegenerative processes are not well-defined. However, evidence indicates that dysregulated expression and/or processing of APP gene products or derivatives of these gene products derivatives are involved in the pathophysiological process leading to neurodegeneration and plaque formation. For example, missense mutations in APP are tightly linked to autosomal dominant forms of AD (Hardy (1994) *Clin. Geriatr. Med.* 10:239–247; Mann et al. (1992) *Neurodegeneration* 1:201–215). The role of APP in neurodegenerative disease is further implicated by the observation that persons with Down's syndrome who carry an additional copy of the human APP (hAPP) gene on their third chromosome 21 show an overexpression of hAPP (Goodison et al. (1993) *J. Neuropathol. Exp. Neurol.* 52:192–198; Oyama et al. (1994) *J. Neurochem.* 62:1062–1066) as well as a prominent tendency to develop AD-type pathology early in life (Wisniewski et al. (1985) *Ann. Neurol.* 17:278–282). Mutations in Aβ are linked to CAA associated with hereditary cerebral hemorrhage with amyloidosis (Dutch (HCHWA-D) (Levy et al. (1990), supra), in which amyloid deposits preferentially occur in the cerebrovascular wall with some occurrence of diffuse plaques (Maat-Schieman et al. (1994) *Acta Neuropathol.* 88:371–8; Wattendorff et al. (1995) *J. Neurol. Neurosurg. Psychiatry* 58:699–705). A number of hAPP point mutations that are tightly associated with the development of familial AD encode amino acid changes close to either side of the Aβ peptide (for a review, see, e.g., Lannfelt et al. (1994) *Biochem. Soc Trans.* 22:176–179; Clark et al. (1993) *Arch. Neurol.* 50:1164–1172). Finally, in vitro studies indicate that aggregated Aβ can induce neurodegeneration (see, e.g., Pike et al. (1995) *J. Neurochem.* 64:253–265).

More recently, the apoE protein has been implicated in Alzheimer's disease (hereafter "AD") and cognitive performance. Saunders et al. *Neurol.* 43:1467–1472 (1993); Corder et al. *Science* 261:921–923 (1993); and Reed et al. *Arch. Neurol.* 51:1189–1192 (1994). Apolipoprotein E (ApoE) is a 34,000 molecular weight protein which is the product of a single gene on chromosome 19. ApoE-containing lipoproteins are found in the cerebrospinal fluid and appear to play a major role in lipid transport in the central nervous system (CNS). Pitas et al. *J. Biol. Chem.* 262:14352–14360 (1987). ApoE mRNA is abundant in the brain, where it is synthesized and secreted primarily by astrocytes. Elshourbagy et al. *Proc. Natl. Acad. Sci USA* 82:203–207 (1985); Boyles et al. *J. Clin. Invest.* 76:1501–1513 (1985); and Pitas et al. *Biochem. Biophys. Acta* 917:148–161 (1987). The liver, followed by the brain, has the highest level of apoE mRNA expression in the human body. In normal brains, the major source of apoE is from astrocytes. The source of apoE in senile plaques, however, remains unclear. El Khoury at al., *Neurobiol. Aging* 19:S81–S84 (1998); Boyles et al., *J. Clin. Invest.* 76:1501–1513 (1985).

ApoE levels dramatically increase (about 250-fold) after peripheral nerve injury. Müller et al. *Science* 228:499–501 (1985); and Ignatius et al. *Proc. Natl. Acad. Sci. USA* 83:1125–1129 (1986). For CNS neuronal repair, regulation appears to occur in response to neuronal injury, although it is not clear whether the apoE secreted in response to injury is produced by neurons or by glia. (Messer-Joudrier et al., *Eur. J. Neurosci.* 8:265–261 (1996).

Human apoE exists in three major isoforms designated apoE2, apoE3 and apoE4 (for review, see Mahley (in press) *Molecular and Genetic Bases of Neurological Disease* 2nd ed.; and Mahley *Science* 240:622–630 (1988)). The different isoforms result from amino acid substitutions at amino acid residue positions 112 and 158. The common isoform, apoE3, has a cysteine residue at position 112 and an arginine residue at position 158. The apoE4 isoform differs from apoE3 only at position 112, which is an arginine residue. The apoE2 isoform, associated with type III hyperlipoproteinemia (Mahley (1988)), differs from apoE3 only at position 158, which is a cysteine residue. ApoE3 and apoE4 bind normally to the low density lipoprotein (LDL) receptor, whereas apoE2 binds weakly.

The apoE4 allele is associated with the two characteristic neuropathologic lesions of AD extracellular neuritic plaques representing deposits of amyloid beta (Aβ) peptide and intracellular neurofibrillary tangles representing filaments of hyperphosphorylated tau, a microtubule-associated protein. For review, see, McKhann et al. *Neurol.* 34:939–944 (1984); Selkoe *Neuron* 6:487–498 (1991); Crowther *Curr. Opin. Struct. Biol.* 3:202–206 (1993); Roses *Curr. Neurol.* 14:111–141 (1994); Weisgraber et al. *Curr. Opin. Lipidol.* 5:110–116 (1994); and Weisgraber et al. *Curr. Opin. Struct. Biol.* 4:507–515 (1994).

There are currently no effective therapies for arresting, preventing and, more importantly, reversing the impairment of central nervous system function once a degenerative cascade begins. Likewise, there is no current therapy for restoration of normal, central nervous system function when the induced stress has a less catastrophic or partially reversible effect compared to the dementias. The effects of events that impair the function of the CNS, such as traumatic brain injury and stroke are in need of such therapies to mitigate or reverse the resulting damage.

SUMMARY OF THE INVENTION

A method is disclosed which comprises: (1) analyzing glial cells (astrocytes and microglial cells) to determine if the cells are expressing apoE and if expression is found; and (2) administering a compound which reduces or completely eliminates apolipoprotein E (apoE) expression by glial cells.

The present invention provides a method of arresting, preventing and/or reversing the impairment of central nervous system function by reducing β-amyloid plaque burden via the administration of compounds that reduce apoE production. Exemplary compounds that can be used in the method of the invention are: 1) inhibitors of 3-hydroxy-3-methylglutaryl coenzyme A (HMG CoA) reductase; 2) inhibitors of cholesterol biosynthesis; 3) inhibitors of protein isoprenylation, preferably inhibitors of gerangeranylation; and/or 4) inhibitors of NF-κB activation or function. The compounds used in the method of the invention, alone or in combination, reduce the release of apoE and thereby reduce the rate of formation of β-amyloid plaque in brain tissue.

In one embodiment of the invention, the compound administered is characterized by an ability to reduce the activity of 3-hydroxy-3-methylglutanyl coenzyme A (HMG CoA) reductase in brain tissue. Preferably, the molecules are compounds in the Statin family, and more preferably the compound is mevastatin, lovastatin, compactin, nisvastatin, atorvastatin, pravastatin, simvastatin, or fluvastatin.

In another embodiment of the invention, the compound administered is characterized by an ability to reduce protein isoprenylation. The compound may reduce protein isoprenylation such as geranylation, famesylation, and more preferably suppresses geranylgeranylation. In one preferred embodiment, the compound suppresses enzymes involved in geranylgeranylatyion, e.g., inhibitors of geranylgeranyl protein transferase (GGPTase) and/or geranylgeranyldipiphosphate (GGPP) synthase.

In yet another embodiment of the invention, the compound administered to reduce the β-amyloid plaque burden in a subject suppresses cholesterol biosynthesis, which reduces the production of apoE in brain tissue of the treated subject. Preferably, the compounds used to suppress cholesterol biosynthesis are inhibitors of biosynthesis and/or the mevalonate pathways.

In yet another embodiment of the invention, the compound administered to reduce the β-amyloid plaque burden in a subject inhibits the activation or function of NF-κB. Such a compound may, for example, inhibit NF-κB directly (e.g., by binding-to the activated molecule), inhibit release of NF-κB by IκB, or inhibit activity of one or more molecules involved the kinase cascade that mediates NK-κB activation and translocation to the nucleus.

An object of the invention is to reduce the level of β-amyloid plaques in the CNS of a mammal by reducing levels of HMG CoA reductase activity, by reducing NF-κB activity, and/or by reducing protein isoprenylation, each of which alone or in combination results in reduced production of apoE in brain tissue. Preferably, the compound used to reduce HMG CoA reductase activity is an HMG CoA reductase inhibitor, and more preferably the compound is in the Statin family or a compound which inhibits protein isoprenylation, e.g., an inhibitor of geranylgeranylation.

Another object of the invention is to treat a subject with an amyloid-associated disorder by administering to the subject a compound that reduces HMG CoA reductase activity, NF-κB activation or activity, or isoprenylation, e.g., geranylgeranylation. This in turn suppresses the release of apoE in the brain, reducing the level of amyloid plaque production in brain tissue. This treatment may be used in any amyloid-associated disorder, preferably CAA or a prion-mediated disorder, and more preferably AD.

A feature of the invention is that it is effective in treating individuals with an ApoE4 allele, but is also effective in treating ApoE3 and ApoE2 individuals.

Another object of the invention is to reduce the formation of amyloid plaques in the brain of a subject at risk for an amyloid associated disorder by administering to the subject a compound that reduces HMG CoA reductase activity. Reduction in HMG CoA reductase activity results in reduced β-amyloid stimulated release of apoE from cells, and preferably reduces release of apoE from glial cells.

Another object of the invention is to prevent the formation of amyloid plaques in the brains of subjects by administering a compound which inhibits isoprenylation of proteins.

Another object of the invention is to prevent the formation of amyloid plaques in the brains of subjects by administering a compound which inhibits NF-κB activation and/or function.

A feature of the invention is that it is particularly effective for people at risk for amyloid disorders due to the presence of the apoE4 allele.

An advantage of the invention is that many of the identified compounds, e.g., HMG CoA reductase inhibitors, are safe for treatment for extended periods of time.

Another advantage of the invention is that compounds of the invention are able to cross the blood brain barrier at concentrations sufficient to elicit a pharmacological effect.

These and other objects, advantages, and features of the invention will become apparent to those persons skilled in the art upon reading the details of the invention as more fully described below.

DETAILED DESCRIPTION OF PREFERRED EMBODIMENTS

Figure 1:
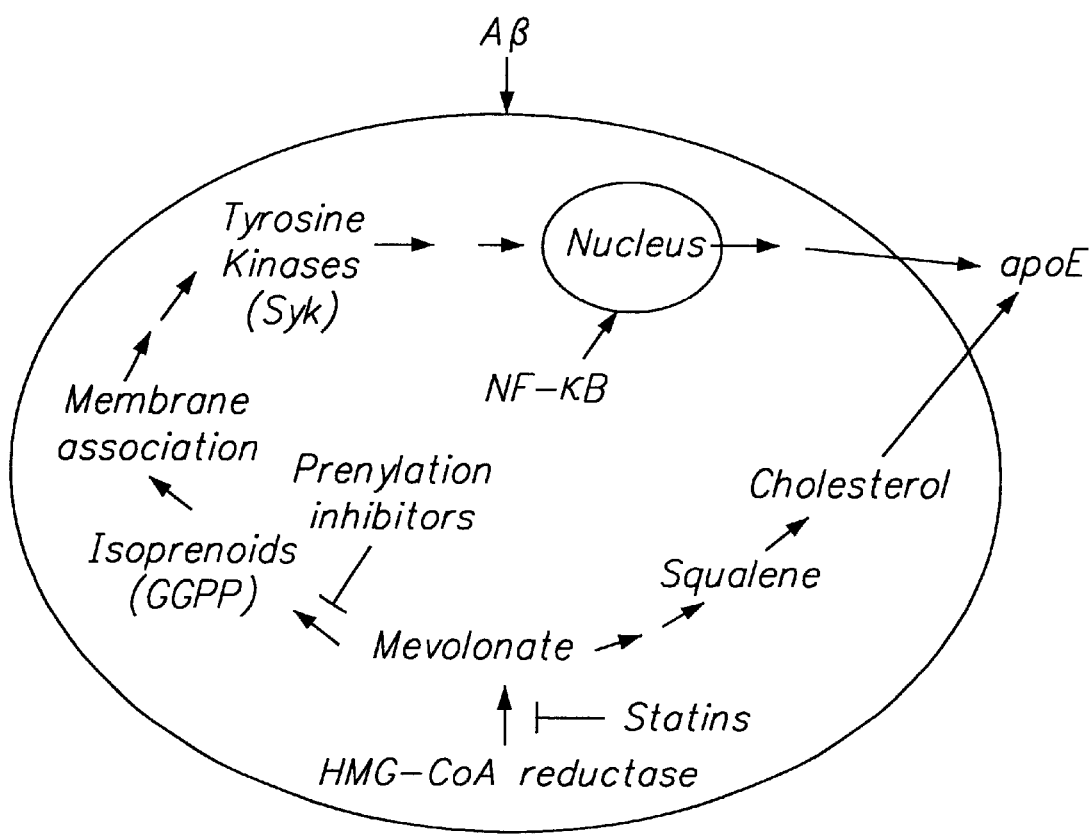
FIG. 1 schematically illustrates two identified mechanisms for Aβ stimulated apoE secretion by microglia.

Before the present methods and compounds are described, it is to be understood that this invention is not limited to particular methods or compounds described and may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a compound" includes a plurality of such compounds and reference to "an AD-type pathology" includes reference to one or more such pathologies and equivalents thereof known to those skilled in the art, and so forth.

All publications mentioned herein are incorporated herein by reference for the purpose of describing and disclosing, for example, the compounds, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention. Further, the publication dates provided may be different from the actual publication date which may require independent verification.

Definitions

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:
  (a) preventing the disease or symptom from occurring in a subject which may be predisposed to the disease or symptom but has not yet been diagnosed as having it;
  (b) inhibiting the disease symptom, i.e., arresting its development; or
  (c) relieving the disease symptom, i.e., causing regression of the disease or symptom.

By "effective dose" or "amount effective" is meant an administration of a compound sufficient to provide the desired physiological and/or psychological change. This will vary depending on the patient, the disease and the treatment. The dose may either be a therapeutic dose, in which case it should sufficiently alter levels of amyloid plaques in the subject to alleviate or ameliorate the symptoms of the disorder or condition, or a prophylactic dose, which should be sufficient to prevent accumulation of amyloid plaques to an undesirable level.

The term "compound" as used herein describes any molecule, e.g. protein or small molecule pharmaceutical, with the capability of affecting the molecular and clinical phenomena associated with amyloid-associated disorders, and specifically AD, CAA, and prion-mediated disorder.

The terms "apoE release", "apoE production," and the like are used to interchangeably herein to include any mechanism by which any isoform of apoE is made available to cells. Thus, the terms cover transcription, translation, and/or release of apoE through a cell membrane.

The term "diagnosis" is used herein to cover any type of analysis used to determine or project a status which includes identification of a disease from its symptoms and determining the presence of molecules (e.g., apoE) in an area (e.g., brain tissue) which suggest a disease status (e.g., beginnings of Alzheimer's disease).

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "amyloid-associated disorder" as used herein refers to a degenerative disorder involving the formation of protein deposits in the brain of a mammal suffering the disorder. The term encompasses, but is not limited to, degenerative diseases such as AD, CAA, prion-mediated disorders, Parkinson's disease, ALS, FTD, Pick's disease, Huntington's disease or CJD.

The term "mammal at risk for an amyloid-associated disorder" as used herein refers to mammals that are predisposed to an amyloid-associated disorder, such as humans genetically at risk for AD, Parkinson's disease, ALS, FTD, Pick's disease, Huntington's disease or CJD. Mammals may also be determined to be at risk due to exposure to infectious agents causing amyloid-associated disorders, e.g. cattle exposed to bovine prions from a BSE contaminated sources or humans.

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing amyloid β protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances.

The term "prion" shall mean an infectious particle known to cause diseases (spongiform encephalopathies) in humans and animals. The term "prion" is a contraction of the words "protein" and "infection" and the particles are comprised largely if not exclusively of $PrP^{Sc}$ molecules encoded by a PrP gene. Prions are distinct from bacteria, viruses and viroids. The term "prion-mediated disorder" refers to any disorder caused by infection with a prion particle. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

General Methodology

A method of treatment is disclosed which comprises: (1) analyzing a patient, or more particularly analyzing glial cells, both microglial cells and astrocytes, from the central nervous system; (2) determining the level of expression of apoE in the patient and more particularly the level of expression of apoE from glial cells; and (3) administering to the patient (and more particularly to the patient's glial cells) an amount of a compound sufficient to reduce or completely eliminate apoE expression in and release by glial cells.

The invention also includes assay methodology for finding compounds which reduce apoE expression in glial cells, both microglial cells and astrocytes. The assay method comprises: (1) culturing glial cells with a known level of expression of apoE; (2) contacting the cultured cells with a compound being tested; and (3) determining the effect of the compound on expression of apoE by the glial cells. It is preferable to run the assay against a control, e.g., where no compound is added to the cell culture and/or where any carrier added with the test compound is added to a culture to determine if a carrier alone effects apoE expression.

Compounds found to inhibit the apoE expression by glial cells can be further assayed in transgenic mice. Compounds which test positive can be used in a specific method of treatment of the invention described below.

The method of treatment is a method of reducing the level of β-amyloid plaque in the brain tissue of a mammalian host by administering a compound which tested positive in the assay described above. In general, such compounds will 1) reduce the activity of 3-hydroxy-3-methylglutanyl coenzyme A (HMG CoA) reductase; 2) reduce protein prenylation, and specifically geranylgeranylation in brain tissue; 3) reduce cholesterol biosynthesis and/or 4) inhibit activation and function of NF-κB. Modulation of these activities result in reduced production of apoE in brain tissue, specifically by glial cells. Prophylactic use is also contemplated for individuals at risk for Alzheimer's disease or CAA such as the elderly and/or individuals carrying known mutations linked to these disorders. Individuals treated may not presently exhibit symptoms but have been subjected to head and neuronal trauma. Prophylactic use of the compounds may also be contemplated for individuals exposed to infectious prions, for example cows exposed to Bovine Spongiform Encephalitis prions or humans exposed to Creutzfeldt-Jakob Disease prions.

Compounds of the Invention

Compounds of the invention may encompass numerous chemical classes, including but not limited to the compounds described herein with known function. Novel methods are provided which employ compounds that are effective in decreasing the level of apoE in mammalian cells. These compounds may be used single, or in combination, and can affect a single activity (e.g., prenylation) or a combination of activities (e.g., prenylation and NF-κB activation).

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

Two specific processes have been identified which are useful in modulating the secretion of apoE by microglial cell: (1) the protein prenylation pathway and (2) activation of NF-κB. Without being bound to any theory, both of these pathways are involved in apoE production in response to Aβ stimulation (see FIG. 1) as well as in basal production of apoE. It is not clear at present how or whether these two pathways are mechanistically linked; thus, combinations of compounds that target each of these pathways may be especially efficacious in the methods of the present invention.

Figure 2:
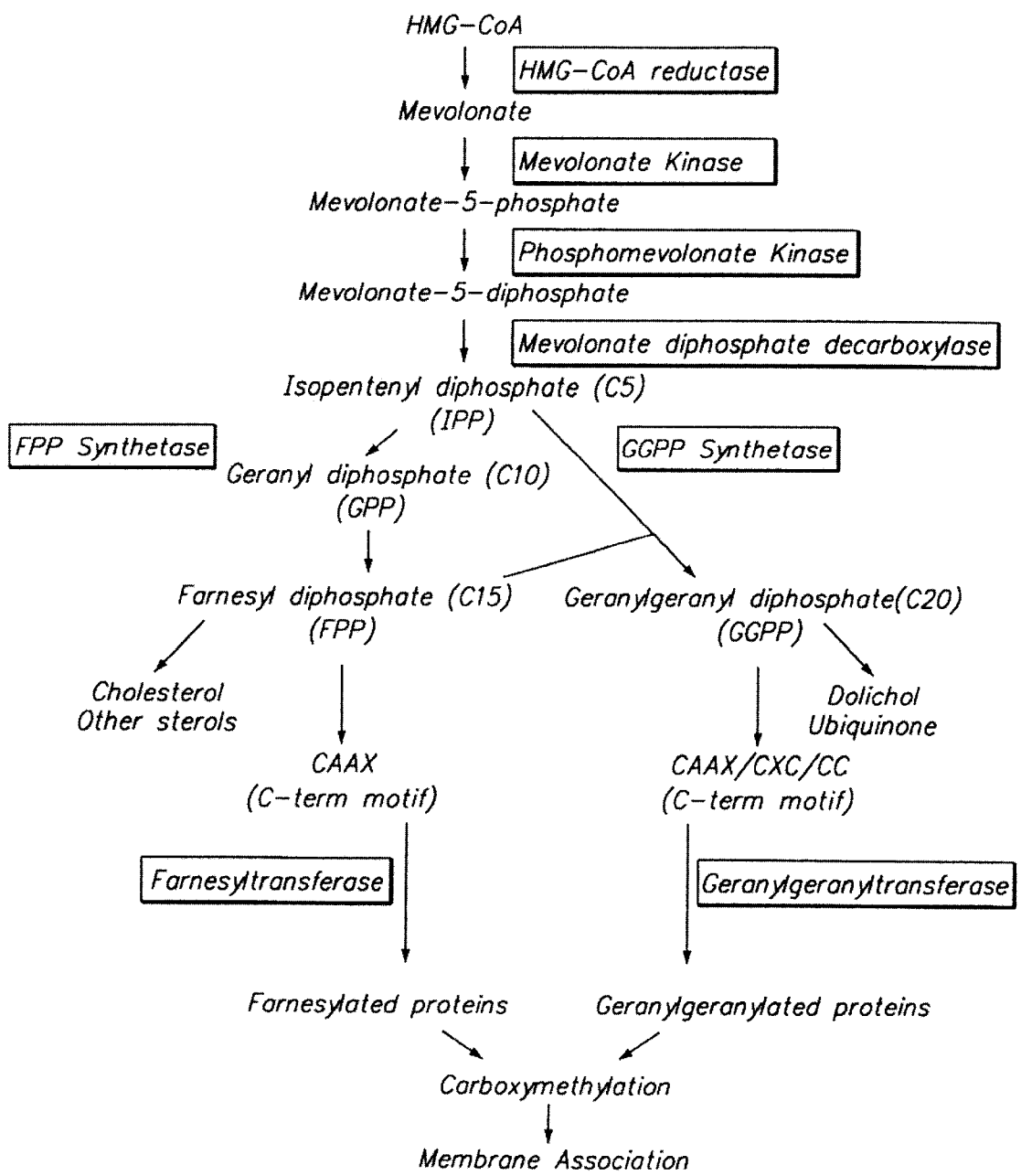
FIG. 2 is an illustration of the molecular cascade of the protein prenylation pathway.

Inhibitors of Molecules Involved in Protein Prenylation and Cholesterol Biosynthesis The characterization of protein prenylation biology and enzymology has opened new areas for the development of inhibitors which can modify physiological processes. The prenylation reactions have been shown genetically to be essential for the function of a variety of proteins (Cox A D, et al. *Biochim Biophys Acta*. 1333:F51–71 (1997); Cox A D, et al. *Curr Opin Cell Biol*. 4:1008–16, (1992); Newman C M, et al. *Biochim Biophys Acta*. 1155: 79–96 (1993); Anant J S, et al., *J Biol Chem*. 267:687–90 (1992)). A number of enzymes have been described in the protein prenylation pathway, and these molecules provide useful targets for modulating apoE production and/or release (see FIG. 2).

Figure 3:
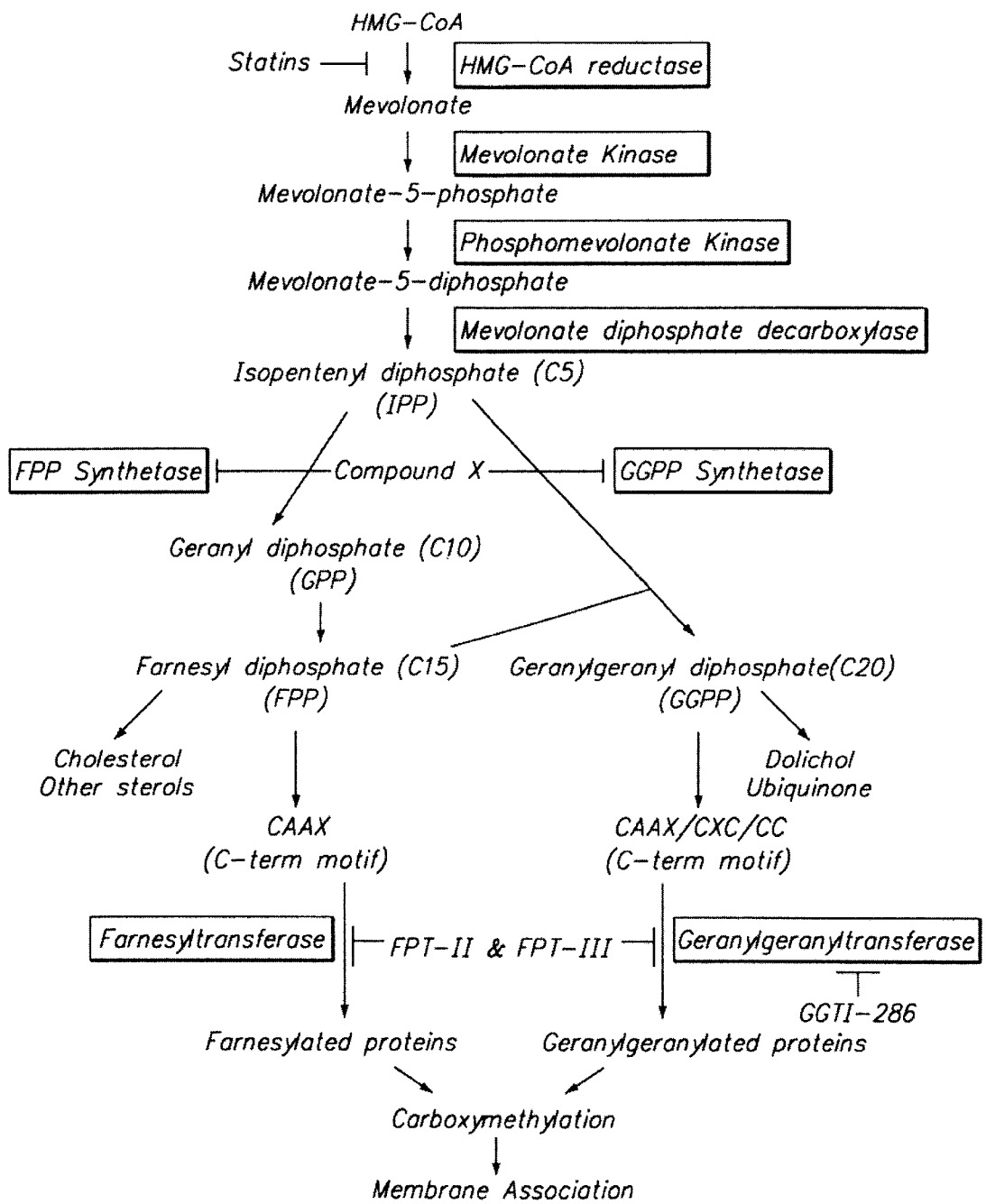
FIG. 3 is an illustration of targets in the protein prenylation pathway that may be inhibited by compounds of the invention to reduce apoE levels and release.

A first category of compounds that reduce apoE levels can be compounds that reduce HMG CoA reductase in mammalian cells. HMG CoA reductase inhibitors of melavonate synthesis may be used in the methods of the invention to reduce β-amyloid plaque burden and/or apoE release. These inhibitors have also been shown, using the assay of the present invention, to modulate apoE levels. A number of HMG CoA reductase inhibitors may be used in the instant invention, including but not limited to mevastatin, lovastatin, compactin, nisvastatin, atorvastatin, pravastatin, simvastatin, and fluvastatin (See FIG. 3).

Cholesterol lowering compounds that inhibit other enzymes in the biosynthetic pathway of cholesterol synthesis may also be used in the method of the invention, either alone or in combination with compounds having other apoE mediating activites. Examples of such compounds include but are not limited to mevalonate pyrophosphate decarboxylase inhibitors, HMG CoA reductase inhibitors, HMG CoA synthase inhibitors, squalene synthase inhibitors, and squalene epoxidase inhibitors. Compounds of interest in the preferred embodiment include lovastatin, simvastatin, pravastatin and fluvastatin.

Other cholesterol lowering compounds that may be used in the invention include niacin, probucol, fibric acids, clofibrate, gemfibrozol and LDL-receptor gene inducers, and zaragozic acid. The additional drugs may be administered separately or in conjunction with the compounds of the invention and may be formulated in the same or a different formulation. Representative of such combinations are those containing about 500–1500 mg of a farnesyl compound in combination with about 20–100 mg of an HMG CoA reductase inhibitor or 250–1000 mg of probucol or 600–1200 mg of gemfibrozil or 1–2 g of clofibrate or 3–6 g of niacin, or 20–300 mg an LDL-receptor gene inducer.

Other compounds that lower apoE production and release can be compounds that inhibit protein isoprenylation, and specifically compounds which inhibit geranylgeranylation of proteins by inhibiting molecules such as geranylgeranyl-dipiphosphate (GGPP) synthase, geranylgeranyl protein transferase (GGPTase), and other enzymes involved in geranylgeranylation. Alternatively or in combination, activity of proteins involved in farnesylation, e.g., farnesyl diphosphate (FPP) synthase and farnesyl protein transferase (FPTase), can be inhibited as well. These therapeutic compounds can block prenylation of proteins, decrease steady state levels of HMG CoA reductase, and block cholesterol synthesis.

Inhibitors of NF-κB Activation

NF-κB is a transcription factor that plays a pivotal role in the highly specific pattern of gene expression observed for immune, inflammatory and acute phase response genes, including interleukin 1, interleukin 8, tumor necrosis factor and certain cell adhesion molecules. Like other members of the Rel family of transcriptional activators, NF-κB is sequestered in an inactive form in the cytoplasm of most cell types. A variety of extracellular stimuli including mitogens, cytokines, antigens, stress inducing agents, UV light and viral proteins initiate a signal transduction pathway that ultimately leads to NF-κB release and activation.

Figure 4:
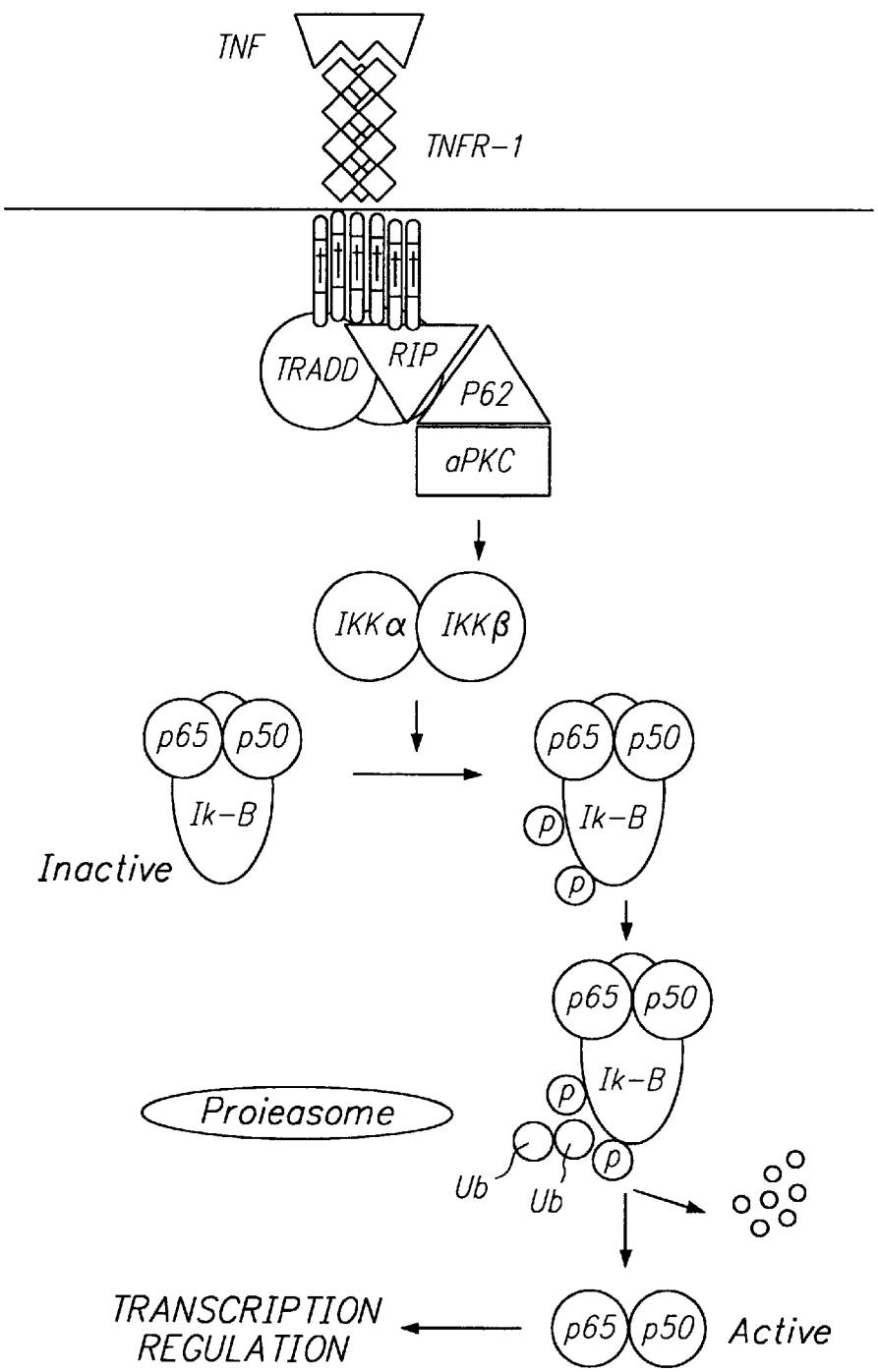
FIG. 4 is an illustration of activation of NF-κB by the kinase cascade and degradation of IκB.

Important modulators of NF-κB activation are the inhibitor proteins IκB$_\alpha$ and IκB$_\beta$ (referred to herein as IκB), which associate with, and thereby, inactivate, NF-κB in vivo. Activation and nuclear translocation of NF-κB occurs following signal-induced phosphorylation of IκB, which leads to proteolysis via the ubiquitin pathway. This pathway includes a cascade of atypical protein kinases that catalyze the ubiquination of IκB, the IκB kinase (IKK) complex (FIG. 4).

Control of NF-κB activation and/or activity may thus be modulated in a number of different ways, including: (1) compounds that activate molecules involved in phosphorylation of IκB, e.g., molecules involved in IKK activity such as IKK-α, IKK-β and NIK (see Karin, *JBC* 274:27339–27342 (1999) and Baeuerle, *Current Biology* 8:R19–R22 (1998)), (2) compounds that increase or accelerate ubiquination of phosphorylated IκB, (3) compounds that prevent migration of activated NF-κB from the cytoplasm to the nucleus; and (4) compounds that bind to NK-κB in the nucleus, preventing interactions between NF-κB and sequences activated by NF-κB binding. Candidate compounds that inhibit apoE production and release can include compounds with known effects on NF-κB activation, such as bacterial lipopolysaccharide, and extracellular peptides and chemical agents that stimulate intracellular kinase activity. Candidate compounds that may be tested in the methods of the present invention can also be identified by screening in other assays for NF-κB activity, such as those described in U.S. Pat. Nos. 5,932,425 and 5,804,374.

Control of NF-κB activation and apoE production can also be determined using a reporter construct with the ability to allow detection of NF-κB activation suppression and/or levels of apoE release. For example, a reporter plasmid DNA bearing a promoter containing NF-κB consensus sites (e.g., consensus sites from the rodent or human apoE gene) joined to a reporter gene can be used to monitor NF-κB activity. Exemplary reporter elements are genes encoding luciferase or β-galactosidase proteins. The promoter-reporter plasmid DNA can be introduced into the glial cells using standard DNA transfection procedures (Sambrook et al., *Molecular Cloning: a Laboratory Manual*, 1989). Selection of stable cell clones harboring the plasmid can be isolated using co-transfection with a plasmid carrying a selectable drug marker or by addition of the selectable drug marker into the promoter-reporter plasmid. A resulting cell clone can then be used to identify compounds which suppress NF-κB activity. Alternatively, transiently transfected cells can be used directly to identify compounds. It may be desirable to first stimulate the cells with β-amyloid, interleukin-6, or another agent to induce the activity of the reporter protein. The cells can be contacted with compounds to identify those which reduce the activity of the reporter activity. Compounds which attenuate NF-κB activity can also be tested for the ability to reduce apoE production from the glial cells.

Administration of the Compounds

In the subject methods, the compound may be administered to the host using any convenient means capable of resulting in the desired target protein activity modulation. Thus, the compound can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, transdermal patches, suppositories, injections, inhalants and aerosols.

As such, administration of the compounds can be achieved in various ways, including oral, buccal, rectal, parenteral, intraperitoneal, intradermal, transdermal, intratracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules. Examples of additives are conventional additives, such as lactose, mannitol, corn starch or potato starch; binders, such as crystalline cellulose, cellulose derivatives, acacia, corn starch or gelatins; disintegrators, such as corn starch, potato starch or sodium carboxymethylcellulose; lubricants, such as talc or magnesium stearate; and if desired, diluents, buffering agents, moistening agents, preservatives and flavoring agents.

The compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol. If desired, conventional additives such as solubilizers, isotonic agents, suspending agents, emulsifying agents, stabilizers and preservatives may also be added. The concentration of therapeutically active compound in the formulation may vary from about 0.5–100 wt. %.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit (e.g., a teaspoonful, tablespoonful, tablet or suppository) contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Compounds for use in the method of the invention may also be small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including, but not limited to: peptides, saccharides, fatty acids, steroids, purines, pyrimidines, derivatives, structural analogs or combinations thereof.

The compounds are added to a host in a physiologically acceptable carrier, at a dosage from 5 mg to 1400 mg, more usually from 100 mg to 1000 mg, preferably 500 to 700 for a dose of 0.5 to 20 mg/kg weight. The dosage for compounds suppressing cholesterol biosynthesis is elected so that the cholesterol biosynthesis is reduced by 10 to 80%, more preferably 20 to 70% and even more preferably 25–50%.

The dosage for compounds inhibiting the activity of HMG CoA reductase is elected so that the HMG CoA reductase activity is reduced by about 20 to 80%, preferably 40 to 50%. The dosage for compounds inhibiting isoprenylation is elected so that the percentage of prenylation of the target molecule is reduced to a suitable level, e.g., geranylgeranylation of HMG CoA reductase is reduced by at least 50%.

ApoE release may be induced by β-amyloid, neuronal injury, response to pharmaceutical compounds, etc. The subject compositions will generally be administered daily, in an amount to provide at least about a 10 to 80%, more preferably 20–70%, even more preferably 25–50% decrease in the release of apoE. Generally, the total daily dosage will be at least about 10 mg, usually at least about 400 mg to 500 mg, preferably about 700 mg, and not more than about 1500 mg, usually not more than about 1000 mg. The amount may vary with the general health of the patient, the response of the patient to the drug, whether the compound is used by itself or in combination with other drugs, and the like. Daily administrations may be one or more times, usually not more than about four times, particularly depending upon the level of drug which is administered.

Assays of Amyloid Pathology

Bioassays

A number of assays are known in the art for determining the effect of a compound on β-amyloid deposition, animal behavior and other phenomena associated with AD and/or CAA. Some examples are provided, although it will be understood by one of skill in the art that many other assays may also be used.

Animal models for Alzheimer's disease may be used to determine the effect of compounds on apoE expression and the extent of β-amyloid deposition. The screening for AD phenotype can include assessment of phenomena including, but not limited to: 1) analysis of molecular markers (e.g., levels of expression of apoE gene products in brain tissue; presence/absence in brain tissue of various apoE variants, isoforms, and mutants associated with AD; and formation of neurite plaques); 2) assessment of behavioral symptoms associated with memory and learning; 3) detection of neurodegeneration characterized by loss of select populations of neurons (neurodegeneration can be measured by, for example, detection of synaptophysin expression in brain tissue or by direct quantitation based on morphology after staining with a neuronal cell body protein such as neurofilament) (see, e.g., Games et al. (1995) Nature 373:523–7). The screening for CAA can include assessment of phenomena including, but not limited to: 1) analysis of molecular markers (e.g., levels of expression of proteins in brain vascular tissue; presence/absence in brain tissue of various apoE variants, isoforms, and mutants associated with CAA; formation of cerebrovascular amyloid deposits); and 2) detection of cerebral hemorrhage associated with amyloid deposition. These phenomena may be assessed in the screening assays either singly or in any combination.

Preferably, the screen will include control values (e.g., the level of amyloid production in the test animal in the absence of test compound(s)). Test substances which are considered positive, i.e., likely to be beneficial in the treatment of AD or CAA, will be those which have a substantial effect upon an AD- or CAA-associated phenomenon (e.g., test agents that are able to reduce the level of Aβ deposition, preferably by at least 20%, more preferably by at least 50%, and most preferably by at least 80%).

Methods for assessing these phenomena, and the effects expected of a compound for treatment of AD and/or CAA, are well known in the art. For example, methods for using transgenic animals in various screening assays for, for example, testing compounds for an effect on AD, are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques).

Pathological Studies

After exposure to the compound, the animals are sacrificed and analyzed by immunohistology for either: 1) neuritic plaques in the brain (AD model) and/or 2) amyloid deposition on cerebrovascular walls (CAA). The brain tissue is fixed (e.g, in 4% paraformladehyde) and sectioned; the sections are stained with antibodies reactive with apoE and/or the Aβ peptide. Secondary antibodies conjugated with fluorescein, rhodamine, horse radish peroxidase, or alkaline phosphatase are used to detect the primary. antibody. These experiments permit identification of amyloid plaques and the regionalization of these plaques to specific areas of the brain.

Sections are also stained with other antibodies diagnostic of Alzheimer's plaques, recognizing antigens such as Alz-50, tau, A2B5, neurofilaments, neuron-specific enolase, and others that are characteristic of Alzheimer's and/or CAA plaques. Staining with thioflavins and congo red can also be carried out to analyze co-localization of Aβ deposits within the neuritic plaques and NFTs of AD or along the vascular walls as in CAA.

Analysis of ApoE Expression 1) mRNA: mRNA can be isolated by the acid guanidinium thiocyanatephenol:chloroform extraction method (Chomczynski et al., (1987) Anal Biochem 162:156–159) from cell lines and tissues of transgenic animals to determine expression levels by Northern blots.

2) In situ Hybridizations: Radioactive or enzymatically labeled probes can be used to detect mRNA in situ. The probes are degraded approximately to 100 nucleotides in length for better penetration of cells. The procedure of Chou et al. (1990) J Psychiatr Res 24:27–50 (1990) for fixed and paraffin embedded samples is briefly described below although similar procedures can be employed with samples sectioned as frozen material.

Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 mu g/mil proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

3) Western Blot Analysis: Protein fractions can be isolated from tissue homogenenates and cell lysates and subjected to Western blot analysis as described by Harlow et al., Antibodies: A laboratory manual, (Cold Spring Harbor, N.Y., 1988); Brown et al.,(1983) J. Neurochem 40:299–308; and Tate-Ostroff et al., (1989) Proc Natl Acad Sci 86:745–749). Only a brief description is given below.

The protein fractions can be denatured in Laemmli sample buffer and electrophoresed on SDS-polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of apoE proteins.

Behavioral Studies of Transgenic Mice and Rats (for AD)

Behavioral tests designed to assess learning and memory deficits can be employed. An example of such as test is the Morris Water maze (Morris (1981) *Learn Motivat* 12:239–260). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. (1997) *Pharmacol Biochem Behav* 57:257–261).

Immunoassays

Immunoassays may also be used to measure β-amyloid induced microglial and astrocyte production of apoE. Antibodies specific for apoE may be used in screening immunoassays, particularly to detect apoE in glial cells, or to qualitatively or quantitatively determine the amount of apoE in a cell or sample. The number of cells in a sample will generally be at least about $10^3$, usually at least $10^4$ more usually at least about $10^5$. The cells may be dissociated, in the case of solid tissues, or tissue sections may be analyzed. Alternatively a lysate of the cells may be prepared.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

EXAMPLES

The following examples are put forth so as to provide those of ordinary skill in the art with a complete disclosure and description of how to make and use the subject invention, and are not intended to limit the scope of what is regarded as the invention nor are they intended to represent or imply that the experiments shown are all or the only experiments performed. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

To identify and characterize inhibitors of apoE secretion and/or production, several methods can be utilized to measure apoE levels, either in vivo or in vitro. Such assays to score apoE could include but are not limited to, an enzyme-linked immuno-sorbent assay (ELISA), Western blot analysis, or immunoprecipitation. The test samples that may be used in the various assays include an aliquot of tissue culture medium conditioned by murine cultured cells, an aliquot of tissue culture medium conditioned by human cultured cells, murine cultured cell extract, human cultured cell extract, plasma from transgenic mice genetically engineered to express any one of the three human apoE isoforms, mouse plasma, human plasma, or human or mouse CSF or tissue extract. The following examples are merely to provide guidance to one skilled in the art as to possible methods for practicing the invention. They are not intended to limit the invention to these particular assays and/or methods of detection.

Example 1

Detection of apoE in a Murine Cultured Cell Extract by ELISA

To detect murine apoE in a murine cultured cell extract, an ELISA is constructed from commercially available antibodies. For example, a goat polyclonal serum raised to the carboxyl-terminus of mouse apoE and a rabbit polyclonal serum raised to the amino-terminus of mouse apoE is purchased from Santa Cruz Biotechnology (Santa Cruz, Calif.) and from BioDesign International (Kennebunk, Me.) respectively. These two antibodies are configured into an ELISA for measuring murine apoE. While incubation times, temperatures and antibody dilution ratios can be adjusted to optimize the ELISA, a basic format for such an assay is performed as follows.

A 96-well microtiter plate is coated with 100 ml of the Santa Cruz Biotechnology (Santa Cruz, Calif.) antiserum diluted to 4 mg/ml in phosphate buffered saline (PBS). The well coating is done overnight at 4° C. The plate wells are washed four times with 200 ml PBS containing 0.05% Tween-20, and then blocked with 100 ml of a 1% bovine serum albumin (BSA) solution made in PBS for 1 hour at 37° C. The wells are then washed four times with 200 ml PBS-0.05% Tween-20. The murine cultured cell extract in a volume of 100 ml is added to the washed well and incubated overnight at 4° C. The murine cultured cell extract can be diluted in PBS with 0.1% Tween-20 or PBS with 0.1% BSA or with a variety of other diluents. Cultured cell extracts are made by any method currently used by those skilled in the art, such as freezing and thawing for several cycles in either PBS or medium. Following incubation of the murine cultured cell extract, the wells are washed four times with 200 ml PBS-0.05% Tween-20 after which 100 ml of a 1:500 dilution (in PBS 0.1% BSA) of the BioDesign International antiserum is added. The plate is incubated for 2 hours at 37° C., and the wells are washed four times with PBS-0.05% Tween-20.

To detect the antibody-apoE complex, 100 ml of a 1:3000 dilution (in PBS-0.1% BSA-0.05% Tween-20) of horseradish peroxidase tagged anti-rabbit IgG is added and the plate incubated for an additional 2 hours at 37° C. Horseradish peroxidase tagged anti-rabbit IgG can be obtained from commercial vendors which sell antibody reagents such as Zymed (Camarillo, Calif.). The wells are next washed four times with 200 ml PBS-0.05% Tween-20. To each well is added 100 ml 3,3',5,5'-tetramethylbenzidine (TMB) substrate to score the peroxidase reaction or the extent of complex formed, i.e., the amount of apoE. The colorimetric reaction of the TMB conversion is monitored visually and when sufficient color development has occurred the reaction is stopped with 100 ml 0.5 N sulfuric acid. The wells are quantitatively scored by scanning the plate at $OD^{450nm}$ using a Spectromax or similar device.

The assay can be standardized to score quantitative amounts of apoE using purified apoE from human or mouse plasma. Purification of apoE can be done using well established procedures such as that described by LaDu et al. in *J. Biol Chem.* 270:9039–9042 (1996); Chiba, Mitamura & Matsumiya in *Biochem. Med. & Metabol. Biol.* 43:53–64 (1990); and Lin *Analyt. Biochem.* 154:316–326 (1986). Briefly, HDL lipoprotein particles are isolated from plasma using standard FPLC fractionation methods. The HDL fraction is dialyzed against 0.01% EDTA, lyophilized and delipidated in $CHCl_3$:MeOH (2:1). Delipidated proteins are pelleted in MeOH and solubilized in 6 M guanidine, 0.1 M Tris-Hcl pH 7.5, 0.01% EDTA and 1% β-mercaptoethanol. Proteins are fractionated on a Sephacryl S-300 column (Pharmacia Biotech Inc.) equilibrated in 4 M guanidine, 0.1 M Tris-Hcl pH 7.5, 0.01% EDTA and 0.1% β-mercaptoethanol. Fractions containing apoE are dialyzed in 5 mM $NH_4HCO_3$, lyophilized and resuspended in 0.1 M $NH_4HCO_3$. Purified apoE can be quantitated by SDS PAGE, protein staining and densitometry.

Example 2

Detection of Human apoE in Human Cultured Cell Extract by ELISA

To detect human apoE, commercial kits are available such as the APO-TEK ApoE™, an apolipoprotein E in vitro diagnostic ELISA, from Perimmune, Inc. The kit method was based on an ELISA using antibodies prepared to purified human apoE protein. Vendor directions were followed to measure human apoE in a human cultured cell extract. Typically the kit can detect free apoE protein as well as apoE on lipoprotein particles.

Example 3

Detection by Western Blot Procedure

An aliquot of tissue culture medium conditioned by human or murine cultured cells is assessed for levels of apoE using Western blot analysis. One such Western blot analysis involves preparing a 4–20% gradient SDS polyacrylamide gel or a 10%–15% SDS polyacrylamide gel. The test sample can be loaded directly onto the gel mixed with gel loading buffer (125 mM Tris-Hcl pH 8.0, 4% SDS, 10% β-mercaptoethanol, 20% glycerol and 0.02% bromphenol blue) or first precipitated with 10% trichloroacetic acid on ice for 30 minutes after which the sample is centrifuged in an Eppendorf and the pelleted protein from the sample washed with 350 ml acetone and reprecipitated. The washed pellet is resuspended in 30–100 ml gel loading buffer. The gel is run at 100–180 volts for 1–2 hours. Protein molecular weight standards are included on the gel to monitor protein separation and transfer. The protein separated in the gel is next transferred to a PVDF membrane (Millipore, Bedford, Mass.) using electrophoresis for 35 minutes at 80 volts in 10% CAPS with 10% methanol. The membrane is removed from the gel and treated with a blocking solution containing non-fat milk and fish gelatin prepared in PBS for 1 hour at room temperature. After blocking the non-specific reactivity of the PVDF membrane with milk and gelatin, the membrane is placed in blocking solution containing apoE antibody. The apoE antibody is typically used at a dilution of 1:500 or 1:1000. For detection of murine apoE, the BioDesign International antiserum is used, and for detection of human apoE, an antibody from Chemicon International can be employed. Other dilutions and other apoE antibodies would likely give equivalent results. The membrane is incubated with rocking for 2 hours at room temperature or overnight at 4° C. After binding the antibody to the membrane, a staining kit can be used to develop the blot, such as the Vectastain ABC kit from Vectastain which uses colormetric detection. Alternatively, chemiluminiscent detection is used. For colormetric detection, the membrane is washed four times for 3 minutes in 100 mm Tris-HCl pH 7.5, 154 mm NaCl (TTBS) with shaking. The membrane is then transferred to a solution containing 5 mg/ml biotinylated second antibody (anti-rabbit or anti-mouse IgG) and incubated for 30 minutes at room temperature. The membrane is washed four times for 3 minutes in TTBS. The membrane is next incubated with a detection system based on a horseradish peroxidase-linked substrate for 30 minutes at room temperature. The membrane is washed four times for 3 minutes in TTBS after which it is transferred to a substrate development solution. The blot is visually developed. When sufficient color reaction has occurred on the blot, the membrane is washed two times for 5 minutes in water and air dried.

Example 4

Detection of apoE by Immunoprecipitation

Human cell culture samples are analyzed for apoE secretion and/or production using immunoprecipitation techniques, and standard methods for immunoprecipitation of proteins are applied. Test samples are mixed for 1 hour with 100 ml of a 10% solution of protein A Sepharose (Pharmacia) after which 5–50 ml apoE human antibody is added. The mixture is incubated at 4° C. overnight with rocking. The mixtures is centrifuged in an Eppendorf at 4000 rpm for 5 minutes. The pellet is washed with 1 ml buffer containing 50 mm Tris-HCl pH 7.5, 0.5 M NaCl, 0.5 mm EDTA and 5% NP40. The pelleting and washing is repeated twice. The pellet is next washed three times with 50 mm Tris-HCl pH 7.5, 150 mm NaCl, 0.5 mm EDTA and 5% NP40. The pellet is washed twice with 1 ml 10 mm Tris-Hcl pH 7.5. The resulting pellet is resuspended in gel loading buffer (50–200 ml), boiled for 5 minutes to release bound protein from the Sepharose beads, and electrophoresed on a 4–20% gradient SDS polyacrylamide gel or a standard 10% or 20% SDS polyacrylamide gel. If samples are radiolabeled with $^{35}$S-methionine/cysteine or with a $^{14}$C-labeled amino acid, the gel can be exposed to film to identify the apoE protein band. Alternatively for unlabeled samples, the gel can be analyzed by the Western blot procedure described above using an apoE antibody.

Example 5

Treatment of Cell Cultures to Test apoE Secretion and Production

Microglial cell lines were used to evaluate changes in apoE expression. Microglial cell lines for use in the method of the invention include murine lines, e.g. BV-2 cell line (Blasi et al. *J. Neuroimmunol.* 27:229–237 (1990) and the N9 cell line (Corradin et al. *Glia* 7:255–262 (1993) or human lines such as those described in Janabi et al. *Neurosci. Lett.* 195:105–108 (1995). The microglial cell lines used were obtained from the investigators who isolated the lines. Astroglial continuous cell lines were also utilized in the assay, e.g. the human U373-MG line or the rodent lines C6 and DI TNC1. All of these astrocytic lines were obtained, from the American Tissue Culture Collection cell repository (Rockville, Md.).

Primary mixed glial cultures, purified primary astrocyte, and purified primary microglial cultures prepared from rodent or human brain tissue (generally fetal) were used in the test assay. A variety of preparation methods can be used to isolate primary glial cultures, both mixed and purified for astroglial or microglial cell types. See e.g. McCarthy and de Vellis, *J. Cell Biol.* 85:890–902 (1980); Levinson & McCarthy in Culturing Nerve Cells, MIT Press, Cambridge, Mass. at 309–336 (1991); Hu et al. *J. Biol. Chem.* 271:2543–2547 (1996); Stone et al. *Exptl. Neurol.* 143:313–318 (1997); Barger et al. *Mol. Brain Res.* 40:116–126 (1996); and Manthorpe et al. *J. Neurocytol.* 8:605–621 (1979). Also, primary glial cultures can be prepared which include neurons, such as in the procedure described by Messmer-Joudrier et al. *Eur. J. Neurosci.* 8: 2652–2661 (1996). For primary cell cultures, different brain regions were used to isolate the cells. Hippocampal, cortical, cerebellar or brain stem cultures were prepared. Primary and continuous cell lines were plated into wells of a multi-well plate at a subconfluent density for the assay. Typically, the cultures were used within 1–2 days of initial plating.

The β-amyloid peptide preparations that were used in the method of the invention were purchased from a variety of commercial sources such as Bachem, QCB, or American Peptide. Different forms of β-amyloid were obtained from vendors including: β-amyloid 1–40 and β-amyloid 1–42, representing the two major forms identified in vivo; and β-amyloid 25–35, an active truncated form. The peptide was used in in vitro experiments to induce apoE secretion/production in two different formats. In the first format, the lyophilized peptide obtained from a vendor was resuspended in PBS or water and used directly to treat cultured cells. Alternatively, the peptide was aggregated prior to treatment of the cell culture. In either approach, the peptide was typically used at concentrations within a range of 30 mM to 100 mm, and therefore stock solutions were generally made to 1 mg/ml and are diluted into culture medium present in the wells of plated cells/tissue.

A number of methods can be used to aggregate the β-amyloid peptide. One method which was used involved resuspending the peptide powder in 50% 1,1,1,3,3,3-Hexafluoro-2-propanol to 1 mm followed by incubation at 37° C. overnight. Aliquots of the peptide were dried in a speed-vac for 1.5 hours. The aliquots are stored at −20° C. To treat cells in culture, aliquots were resuspended in water and placed at 37° C. for hours to days to allow aggregation. The peptide was sonicated for 30 seconds in an ice bath prior to using in an assay.

To screen for inhibitors of apoE secretion or production using cultured brain cells, wells containing cultures were incubated in serum-free medium or medium containing reduced serum concentrations (1 to 0.1%) for various periods of time anywhere from 1–72 hours in the presence of the test compound. For some inhibitors, such as HMG CoA reductase and farnesylation inhibitors, pre-treatment of the cultures with the compound for 4–16 hours in serum-containing growth medium was used to maximize the effectiveness of the assay. Cultures were treated with β-amyloid to stimulate apoE levels in the test paradigm. For tests involving inhibitors which block the induction of apoE secretion by β-amyloid peptide, the peptide was added to the culture when the cultures were placed into low or serum-free medium with the test compound. The apoE secreted by BV2 cells after 4 hour exposure to various doses of aggregated β-amyloid peptide increases with the amount of β-amyloid peptide used, ranging from 0.04 mm to 25 mm.

Figure 5:
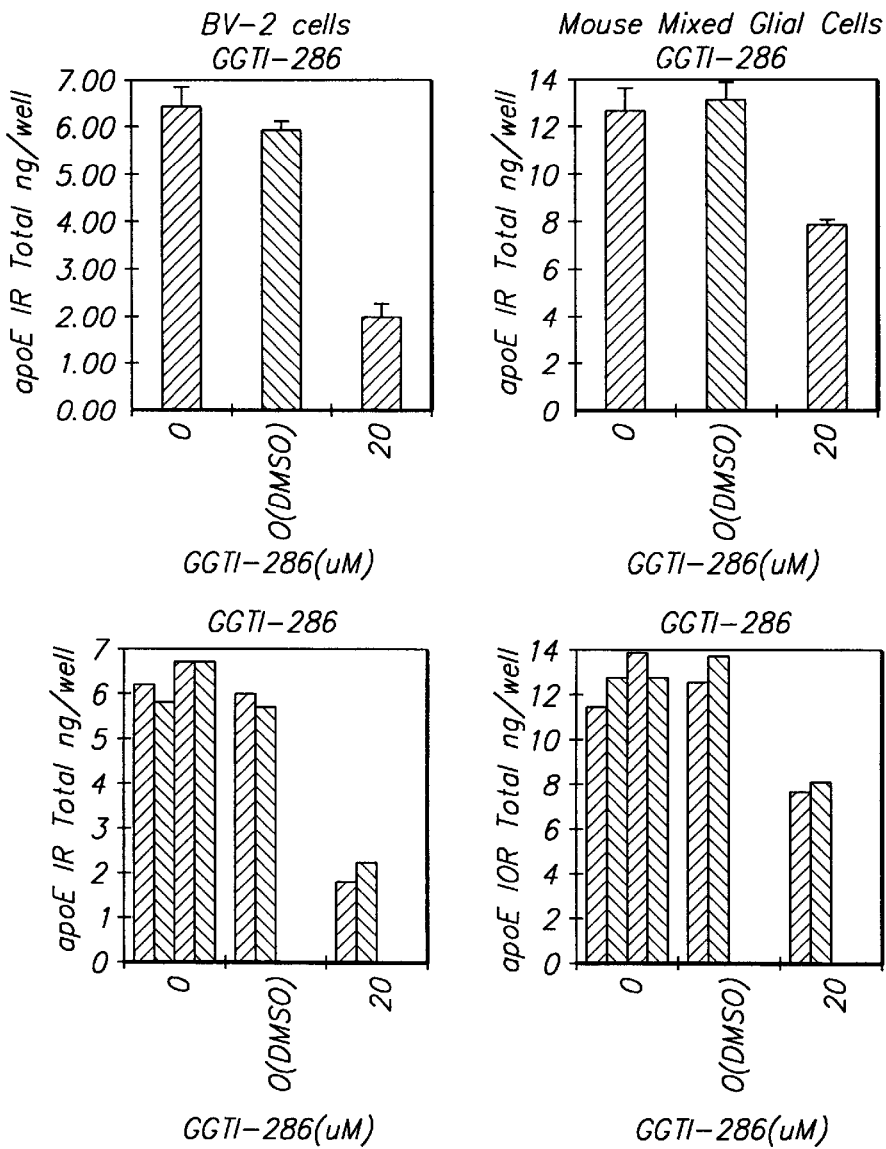
FIG. 5 is a bar graph showing results of inhibition of apoE secretion by GGTI-286. The top two panels show means of collective results, while bottom two panels show individual values.

Using a modification of this test paradigm, inhibitors can also be tested for blocking basal levels of apoE production from cultured glial cells. This is in contrast to using β-amyloid peptide (or another stimulus such as interleukin-6) to induce apoE levels. Cultures were prepared and treated in the same fashion except that β-amyloid treatment was omitted. FIG. 5 shows the inhibitory effects of a geranylgeranylation inhibitor, GGTI-286 (commercially available from CalBioChem), on both BV-2 microglial cells on murine mixed primary glia. For both cell cultures, the geranylgeranylation inhibitor reduced basal apoE levels.

Example 6

Testing Compounds that Reduce HMG CoA Reductase with Organotypic Brain Slice Cultures In general, apoE reducing compounds can be identified by an assay that examines the ability of a compound that suppresses HMG CoA reductase activity to reduce apoE production while preserving cell viability. One method of screening for such compounds is through the use of organotypic brain slice cultures.

Preparation of Cultures.

Eight day old neonatal rat or mouse pups were quickly decapitated with scissors, serrated on one edge, in an aseptic fume hood. The brain was rapidly removed to buffered dissection media containing 100 ml MEM, 1 ml penicillin/streptomycin, 1 ml Tris 100×stock (10 mm final, pH 7.2), sterile filtered and chilled. The hippocampi and cortices were isolated under a dissecting microscope and transported in dissection media to a sterile fume hood. Tissue was positioned on the stage of a MacIllwain tissue chopper with a sterile paint brush, and 400 μm sections were made. Approximately 30 sections per animal were be obtained. Sections were separated by vigorously swirling the petri dish containing the sections in culture media, containing 25% horse serum, 25% Hank's media, 50% minimal essential media, 1 ml penicillin/streptomycin, 0.5 ml L-glutamine. Sections were inspected with a dissecting microscope and damaged tissue removed. The selected sections were manipulated in drops of dissecting media with Pasteur pipettes which had been scored and broken, then fire polished, to produce appropriate diameter bores, and placed on Millipore culture plate inserts set into 35 mm plate containing 1 ml culture media or 6 well plates containing 1.2 ml culture media. Plates containing inserts and media had been pre-equilibrated to 37° C. and 5% $CO_2$. Three to six slices were positioned on each insert. Excess media was drawn off the slice, and the culture placed in a 37° C., 5% $CO_2$ incubator. Cultures were maintained for up to 3 months. Media was changed at 24 hours, and at 3–4 day intervals.

Any mammal can be used as a tissue source for the explant that is used to generate the organotypic brain slice culture used in the present method, so long as the animal can serve as a tissue source and the organotypic slice culture can be established and maintained for a period sufficient to conduct the present methods. Such mammals include, but are not limited to, rats, mice, guinea pigs, monkeys, and rabbits.

The mammal used as a tissue source can be a wild-type mammal or can be a mammal that has been altered genetically to contain and express an introduced gene. Preferably, the animal will be a transgenic animal, such as a transgenic mouse that has been altered to express the human β-amyloid precursor protein or a human apoE variant.

Characterization of cultures.

Organotypic brain slice cultures were inspected daily for the first week in culture and every few days thereafter. During the first week, organotypic brain slice cultures flatten and spread, although tissue architecture is retained. Growth cones were observed emerging from the edge of the slices, and glial cells appeared at the edge of the slice during the first week. Growth cones were subsequently retracted. Glial cells remained at the edge of slices but did not grow over the body of the slice. Cellular organization and composition were assessed in slices which had been maintained in culture for one week intervals from 1 to 8 weeks to confirm that cellular morphology, composition, and organization resembled that of the intact hippocampus.

Organotypic slice cultures were manipulated on the culture insert. The insert was moved using tweezers between culture plates containing the appropriate treatment. First, media was washed from the culture with several rinses of phosphate buffered saline PBS: (100 mM NaCl, 10 mM $NaPO_4$ pH 7.4). Tissue was fixed by incubation for 2 hours at room temperature with freshly prepared 4% paraformaldehyde in PBS. Fix was removed with 2×2 minute rinses in PBS. Endogenous peroxidase activity was quenched by 30 minute room temperature incubation with 0.3% hydrogen peroxide, rinsed 10 minutes in PBS and 10 minutes in PBS with 0.2% gelatin. Next they were blocked in PBS/10% goat serum/0.1% Nonident P-40 for one hour and rinsed 2×10 min in PBS. Primary antibody was applied at the indicated dilution made in PBS containing 0.2% gelatin and incubated overnight in a humidified chamber. After 3×3 minute rinses in PBS/gelatin, cultures were incubated with a 2° antibody, (either anti-mouse or anti-rabbit as appropriate, provided with Vectastain Elite immunohistochemistry kit) in PBS/ gelatin at 37° C. for 30 minutes. Vectastain Elite ABC reagent was prepared according to manufacturer's instructions. Following 3×3 minute rinses with PBS/0.2% gelatin, cultures were incubated at 37° for 30 minutes with the ABC reagent. Immunoreactivity was visualized by development with a 3,3'-diaminobenzidine (DAB) kit from Vector labs and prepared according to directions and rinsed with water. Dehydration was accomplished by 2 minute incubations in 35%, 50%, 70%, 90%, and 2×100% ethanol. Cultures were counterstained for 2–4 minutes with hematoxylin, and rinsed with water until clear. Destaining of insert itself with 0.5% hydrochloric acid in 70% ethanol for 30 sec and tap water rinses followed. After air drying, individual slices were cut out of the insert and mounted on microscope slides using gel mount, covered with cover slips and sealed with nail polish.

Cresyl violet, hematoxylin, and toluidine blue staining were performed by fixing cultures in paraformaldehyde as described above. Hematoxylin (Sigma) was applied for 2–4 minutes, after which cultures were rinsed with water and cleared in ethanol as described above. Cresyl violet and toluidine blue were made as stock dye solution of 0.1% in distilled water. Staining solution was made as 20% in 0.2 M acetate buffer, pH 4.45: 3 parts 0.2 M acetic acid, 2 parts 0.2 M sodium acetate, 5 part water. Staining time was 20 minutes for both dyes. Cultures were rinsed with water, dehydrated in ethanol, dried, and mounted as described above.

Testing with Compounds.

Compounds that were known to reduce HMG CoA reductase activity were dissolved in DMSO to produce 100×stock solutions. Stocks were further diluted in culture media to give final concentrations of 0.1 $\mu$M, and 100 $\mu$M compound. Media was pre-equilibrated in plates at 37° C., 5% $CO_2$. Culture inserts holding 3 rat organotypic brain slices obtained from 8 day old animals and maintained in culture for 2 weeks were transferred to the media containing test solution. Media was collected and fresh media containing test solution provided at 24 hour intervals for 1–10 days. Organotypic brain slice cultures were observed daily for integrity.

After treatment, medium is harvested and assayed for apoE levels using immunoassays such as ELISA or Western blot. Cell lysates prepared from the treated brain slices and analyzed for cell-associated apoE using the same assays.

Example 7

Figure 6:
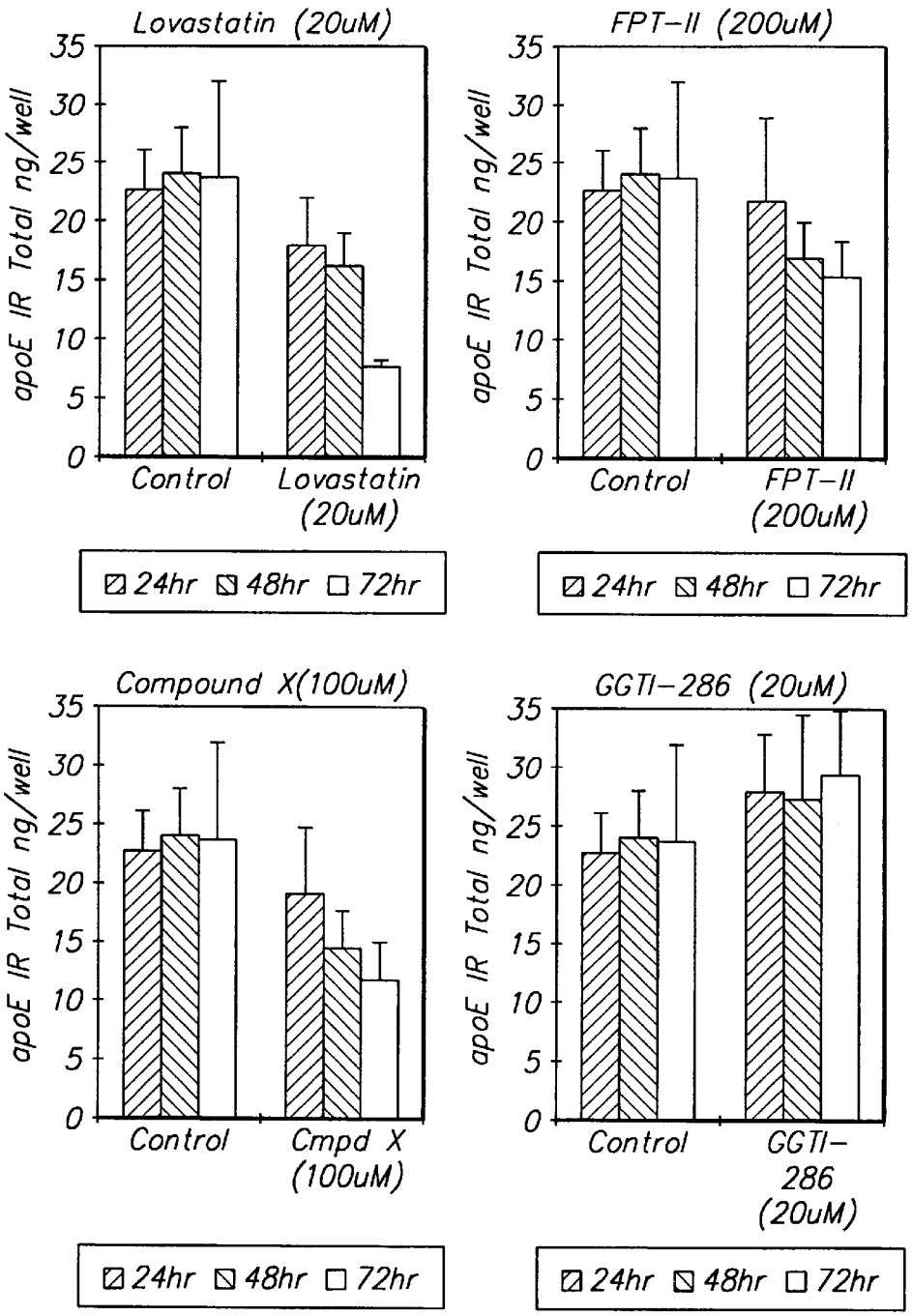
FIG. 6 is a bar graph illustrating the effect of various inhibitors on apoE secretion in Hippocampus slices. Data shows means of quadruplicate experiments.

Testing Compounds that Reduce Protein Isoprenylation or NF-κB Activation with Organotypic Brain Slice Cultures ApoE reducing compounds may also be identified by an assay that examines the ability of a compound that suppresses protein isoprenylation or NF-κB activation to reduce apoE. The method used to assess the activity of known and potential isoprenylation suppressers, in particular geranylgeranylation inhibitors, or potential suppressors or activation NF-κB is generally carried out as per Example 6. FIG. 6 shows the inhibitory effect on apoE release from organotypic hippocampal cultures after contact with the HMG-CoA reductase inhibitor, lovastatin, with a non-specific farnesylation inhibitor which also inhibits geranylgeranylation, FPT-II, with Compound X, an inhibitor of geranylgeranyl diphosphate, and with a selective geranylgeranylation inhibitor, GGTI-286. These graphs display the effects of each drug at 24, 48, 72 hours after treatment from the three individual 24 hour treatment periods.

Figure 7:
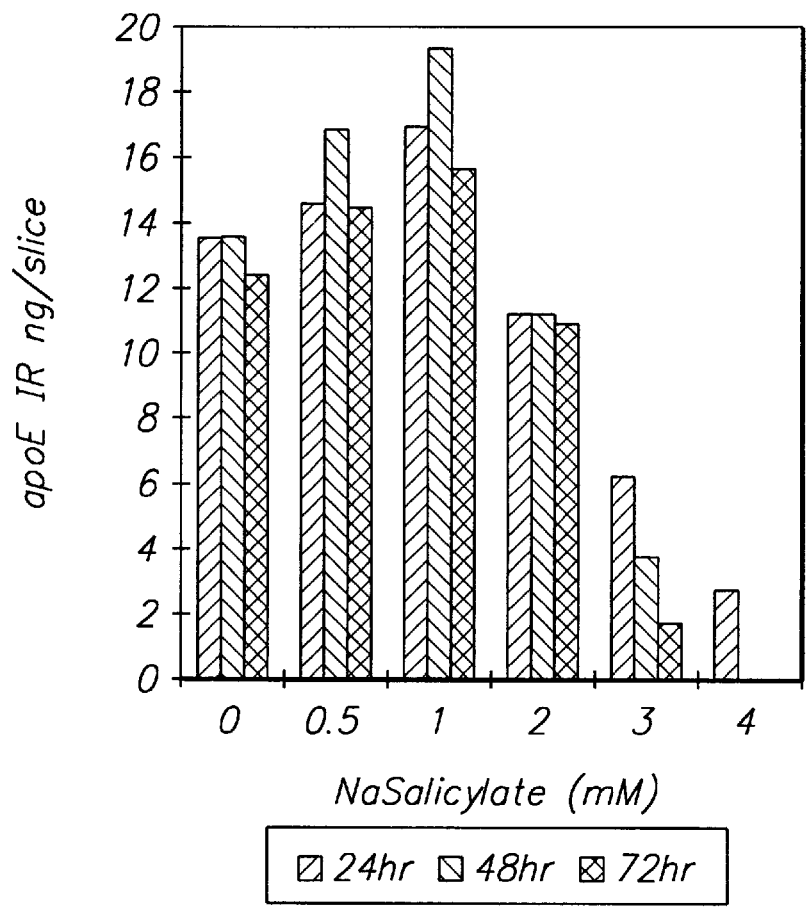
FIG. 7 is a bar graph illustrating dose dependent inhibition of apoE by NaSalicylate in Hippocampus slices.

In support of inhibiting NF-κB activation as a means to block apoE production, organotypic hippocampal brain slice cultures were treated with sodium salicylate, an inhibitor of one of the kinases which activates NF-κB. The results shown in FIG. 7 demonstrate both a time- and dose-dependent inhibition of apoE in the brain culture paradigm.

Example 8

Testing Compounds that Reduce NF-κB Activation

Glial cell lines or primary glial cultures as described in Example 5 are used to identify compounds which attenuate NF-κB activation and apoE production. A reporter construct directed by a trimeric NF-κB motif (see Kastenbauer S, et al. Infect Immun. 67:1553–9 (1999)) is introduced into the glial cells using standard DNA transfection procedures, and cells expressing this vector selected using antibiotic resistance. Cells expressing the construct are then used to identify compounds which suppress NF-κB activity.

Cells expressing the reporter construct are stimulated with β-amyloid to induce the activity of the reporter protein. The cells are then contacted with candidate compounds to identify those which reduce the activity of the reporter activity. Compounds which are found to attenuate NF-κB activity are subsequently tested for their ability to reduce apoE production from the glial cells.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. An assay to identify a compound that downregulates apolipoprotein E expression in a glial cell comprising the steps of:

culturing glial cells which express apolipoprotein E at a known level;

contacting the cells with a compound to be tested;

comparing apolipoprotein E expression of the glial cells in contact with the compound with apolipoprotein E expression in a control culture that is not in contact with the compound;

determining effects of the compound on the apolipoprotein E expression; and identifying said compound that downregulates apolipoprotein E expression, wherein the compound to be tested suppresses NF-κB activation, and wherein suppression is identified using an NF-κB reporter construct.

2. An assay to identify a compound that downregulates apolipoprotein E expression in a glial cell comprising the steps of:

culturing glial cells which express apolipoprotein E at a known level;

contacting the cells with a compound to be tested;

comparing apolipoprotein E expression of the glial cells in contact with the compound with the known levels of apolipoprotein E expression;

determining effects of the compound on the apolipoprotein E expression; and identifying said compound that downregulates apolipoprotein E expression, wherein the compound to be tested suppresses NF-κB activation, and wherein suppression is identified using an NF-κB reporter construct.

* * * * *